(12) United States Patent
Chang (10) Patent No.: US 6,517,349 B2
(45) Date of Patent: Feb. 11, 2003

(54) MANUAL HAND RATCH REAMER FOR DENTIST

(76) Inventor: Sang Kohn Chang, A-216 Dalsung Mansion, 55-68 Daebong 1-Dong Jung-gu Taegu (KR)

( * ) Notice: Subject to any disclaimer, the term of this patent is extended or adjusted under 35 U.S.C. 154(b) by 0 days.

(21) Appl. No.: 09/827,308

(22) Filed: Apr. 6, 2001

(65) Prior Publication Data

US 2002/0034716 A1 Mar. 21, 2002

(30) Foreign Application Priority Data

Apr. 6, 2000 (KR) .......................................... 2000-17882

(51) Int. Cl.[7] .................................................. A61C 3/00
(52) U.S. Cl. ...................................... 433/141; 433/144
(58) Field of Search ................................. 433/141, 112, 433/114, 144, 102; 606/80

(56) References Cited

U.S. PATENT DOCUMENTS

| | | | | |
|---|---|---|---|---|
| 797,106 A | * | 8/1905 | Gray | 433/141 |
| 879,254 A | * | 2/1908 | Gauthier | 433/141 |
| 1,198,628 A | * | 9/1916 | Ebenreiter | 433/141 |
| 3,906,636 A | * | 9/1975 | Rainey et al. | 433/102 |
| 5,941,705 A | * | 8/1999 | Makris et al. | 433/141 |

* cited by examiner

Primary Examiner—Cary E. O'Connor
(74) Attorney, Agent, or Firm—Jacobson Holman PLLC

(57) ABSTRACT

Disclosed is a manual hand ratch reamer for a dentist, which is used for forming a cylindrical hole in an alveolar bone of a patient upon implementing a dental implantation surgery. The manual hand ratch reamer for a dentist comprises a front piece body, a rear piece body and a rotating driver which are connected one with another in a manner such that the rotating driver can be independently rotated with respect to the front piece body and the rear piece body. A reamer tip locking section of the rotating driver, to which a reamer tip is secured, includes a connection device which is connected to the rotating driver by passing through the inside of the front piece body. When the rotating driver is rotated with respect to the front piece body, the front piece body is prevented from being rotated.

9 Claims, 7 Drawing Sheets

MANUAL HAND RATCH REAMER FOR DENTIST

BACKGROUND OF THE INVENTION

1. Field of the Invention

The present invention relates to a manual hand ratch reamer for a dentist, and more particularly, the present invention relates to a manual hand ratch reamer for a dentist, which is configured in such a way as to be suited to dental treatment or dental surgery.

2. Description of the Related Art

A variety of dental implant systems which are installed in a diversity of ways and have numerous effects, are currently known and available in the art. These dental implant systems are installed in a manner such that a dental implant is inserted into an alveolar bone, and, after the dental implant and the alveolar bone undergone osseointegration with each other, an abutment is coupled to the dental implant so as to support the mounting of a prosthetic tooth.

In this regard, conventional dental implant systems are divided into a screw type and a non-screw type. Screw type dental implant systems are described in U.S. Pat. Nos. 4,330,891, 4,763,788, 4,824,372, 5,064,375, 5,064,425, 5,069,622, 5,080,589, 5,098,293, 5,125,841, 5,145,371, 5,154,612 and 5,269,685.

The conventional dental implant system comprises a dental implant, an abutment and a coping. The dental implant is formed, on a circumferential outer surface thereof, with a self-tapping screw, is inserted into an alveolar bone and undergoes osseointegration along with the alveolar bone. The abutment is threadedly coupled to the dental implant on a circumferential inner surface thereof. The coping for a synthetic prosthesis is joined to the abutment by a fastening screw of the synthetic prosthesis.

Consequently, in order to install the dental implant system in the alveolar bone of a patient, a cylindrical hole must be necessarily defined in the alveolar bone. In this connection, the present applicant disclosed a dental implant system in International Patent Application No. PCT/KR00/00050 dated Jan. 24, 2000. Repeatedly speaking, in order to effectuate dental treatment through the dental implant systems which include one diclosed in the international application, a work for forming a cylindrical hole in the alveolar bone must be necessarily performed.

As a dental implement which is employed for this purpose, a ratch reamer which is a kind or handpiece, is known in the art. Conventional hand ratch reamers are driven by fluid injection force or fluid flowing force, or use as their power sources electric motors.

The conventional hand ratch reamers are employed in a manner such that torque is multiplied, using rotating force generated by fluid injection or by the electric motor, through reduction gears which are disposed in the reamers. However, these conventional hand ratch reamers are encountered with a drawback in that they are expensive and apt to be broken. In the case that a breakdown of the electric motor is caused while installing the conventional implant system, specifically, at the place of a molar tooth of upper or a lower jaw, it is difficult to form a cylindrical hole in the alveolar bone, with existing straight type hand ratch reamer, due to a geometrical limitation. In this connection, by the fact that the hand ratch reamer cannot be adequately erected in a vertical direction at the place of molar tooth, a bent type hand ratch reamer which has a bent configuration, is necessarily needed.

Further, when reaming a bone such as a lower jawbone which has a high bone density, the likelihood of the conventional hand ratch reamer to be broken is increased.

In an attempt to solve these drawbacks, hand ratch reamers which can be purchased at a low cost and can be manually rotated to form the cylindrical hole in the alveolar bone, are disclosed in the art. Tie hand ratch reamers have been widely used throughout the world in that diverse implant manufacturers provide hand ratch reamers of shapes and constructions suited to their products.

However, the conventional manual hand ratch reamer suffers from defects as described below, in that a reamer tip is threadedly secured to a fixed cap which is formed with a threaded portion and the entire handpiece is rotated to perform the cylindrical hole forming work.

(1) In the case that the reamer tip is rotated to perform the cylindrical hole forming work in a state wherein the reamer tip is mounted to the fixed cap which is located at a distal end of the handpiece, since an entire body section of the handpiece is rotated, the lips of a patient are liable to be mechanically damaged. Also, as the cylindrical hole forming work is repeatedly performed, the patient feels pain, whereby reluctancy for dental implantation surgery is increased.

(2) Also, since an allowable rotation angle of the manual hand ratch reamer is restricted to a certain value by a geometrical figure of the oral cavity, inconvenience is induced upon installing the dental implant system. Further, since the handpiece in which the end tip has the bent configuration for improving convenience upon implementing the dental implantation surgery, is seriously limited in its use, bothersomeness is imposed on the patient and a dentistry provider.

(3) In the conventional construction, due to the fact that a separate provision for raising rotating force does not exists, a great deal of force is required upon forming the cylindrical hole in the alveolar bone.

(4) As the reamer tip is threadedly coupled with the end cap, when considering the fact that reamer tip of a multitude or sizes are prepared and the dental implantation surgery is implemented while frequently changing the reamer tip, a time required for changing the reamer tip is increased, and thereby, a whole time required for implementing the dental implantation surgery is lengthened.

Figure 6A:
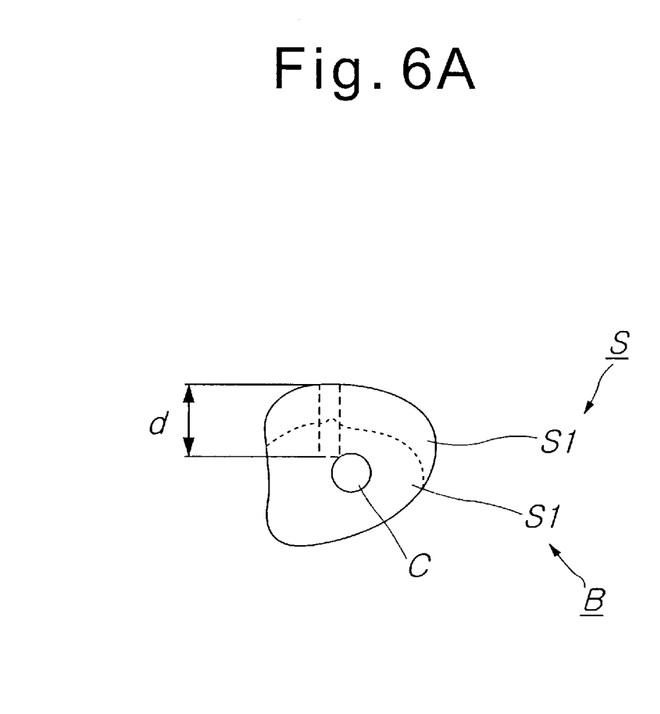
FIG. 6A is a cross-sectional view of a lower jawbone schematically illustrating a state wherein the manual hand ratch reamer for a dentist according to the present invention is used so as to define a cylindrical hole in the lower jawbone.

FIG. 6A illustrates an exemplary dental implantation surgery to which a manual hand ratch reamer is applied. As can be readily seen from FIG. 6A, a lower alveolar bone S1 of a lower jawbone B serves as a portion which constitutes a socket for supporting natural teeth on a mandible B1. As shown in FIG. 6A by a dotted line, a phenomenon in which the lower alveolar bone S1 is gradually absorbed into the mandible B1 due to pathology, occurs. According to this, by the fact that a possible insertion depth for anchoring a dental implant I is decreased, in he case of a patient who has a shallow depth of a lower alveolar nerve canal C or undergoes lapse of a lengthy period of time after one or more natural teeth came out, it is almost impossible to implement dental implantation surgery.

Thus, in order to install a dental implant system, a bone graft procedure must be executed in advance in an attempt to increase a possible insertion depth d for anchoring the dental implant I.

Figure 6B:
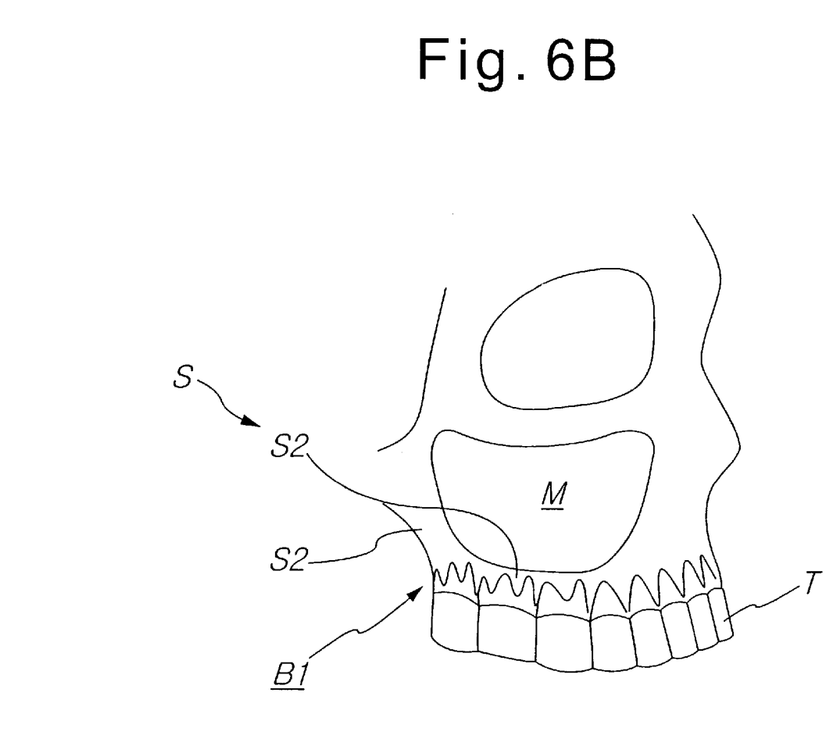
FIG. 6B is a side view of an upper jawbone, for exemplifying limitations which can be induced upon anchoring a dental implant to the upper jawbone.

Specifically, this problem becomes more serious in the case of an upper jawbone B shown in FIG. 6B. In other words, since maxillary sinuses M are respectively defined in the upper jawbone B at both sides of the human face, particularly, a depth of a maxilla B2 which is positioned below the maxillary sinus M, is so small that an upper alveolar bone S2 cannot be properly distinguished. Hence, with the conventional dental implant system, it is difficult to secure a sufficient depth for anchoring the dental implant I.

In particular, in the case of the upper jawbone B, once natural teeth T came out, neumatization of a portion of the upper jawbone B which is located beneath the maxillary sinuses M, takes place as shown in FIG. 2B by a dotted line. By this, since the possible insertion depth for anchoring the dental implant I, is further decreased, the above-described problem is more worsened with the lapse of time after natural teeth T came out.

According to this, in the conventional art, if the bone, that is, the alveolar bone S of the upper or lower jawbone B does not have a sufficient height for enabling the dental implant I to be inserted therein, it is the norm that a bone graft procedure or a maxillary sinus lift procedure in which bone of another part of the human body or synthetic bone is inserted into the lower jawbone B1 or mucosae of the maxillary sinuses M, is executed before anchoring the dental implant I. However, because the dental implant I cannot be anchored in the jawbone until a time of six months to one year is lapsed after the bone graft procedure or maxillary sinus lift procedure is executed and thereby the inserted bone is completely joined to the mandible or maxilla B, a disadvantage is provoked in that huge burden is imposed on a patient in terms of time and cost.

Figure 7:
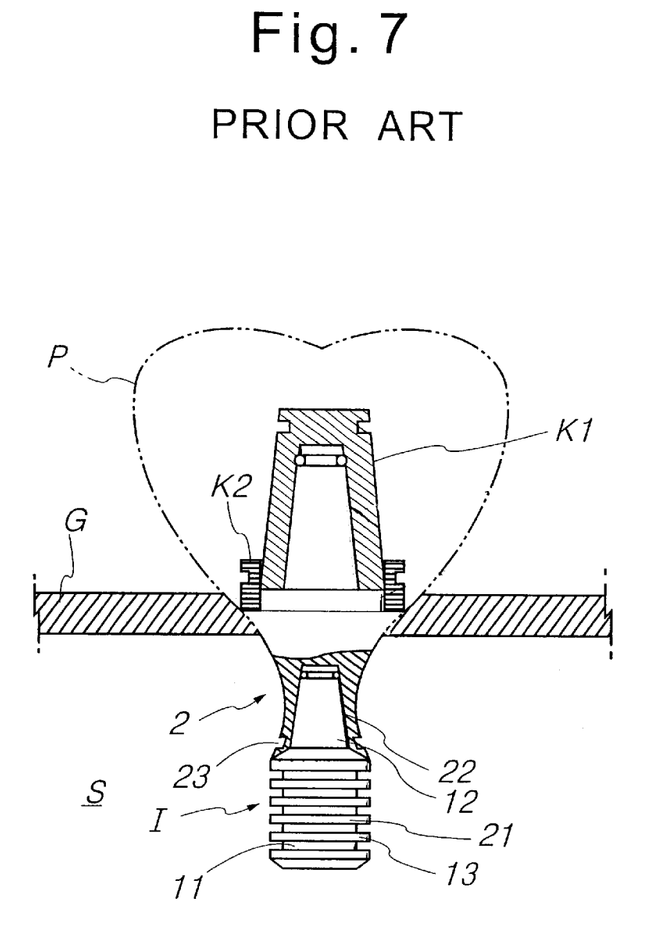
FIG. 7 is a cross-sectional view illustrating an exemplary construction of a dental implant system which is installed using the manual hand ratch reamer for a dentist according to the present invention.

To cope with this disadvantage, the present applicant disclosed a dental implant system as shown in FIG. 7 in International Patent Application No. PCT/KR00/00050. Referring to FIG. 7, the dental implant system comprises a dental implant 1 and an abutment 2. First, the dental implant 1 is composed of a vertical body 11 which has anchoring means such as fins 13 or the like for improving coupling force between the dental implant 1 and an alveolar bone S, and a tapered post section 12 which extends upward from an upper end of the vertical body, 11.

On the other hand, the abutment 2 possesses, on a circumferential inner surface thereof, a socket 22 which has a tapered portion corresponding to the tapered post section 12. The abutment 2 further possesses, on a circumferential outer surface thereof, a body 21 which is defined with anchoring means such as an engaging groove 23 or the like.

Here, the engaging groove 23 which is defined on the circumferential outer surface of the abutment 2, allows a portion of the alveolar bone S to grow into the engaging groove 23 when the abutment 2 and the alveolar bone S experience osseointegration with each other, thereby to increase coupling force between the abutment 2 and the alveolar bone S.

Upon installing the dental implant system, a cylindrical hole must be necessarily defined in the alveolar bone. In order to define the cylinder hole, so far, handpieces adopting a variety of mechanical driving schemes or hand ratch reamers for manual operation have been employed.

Figure 1:
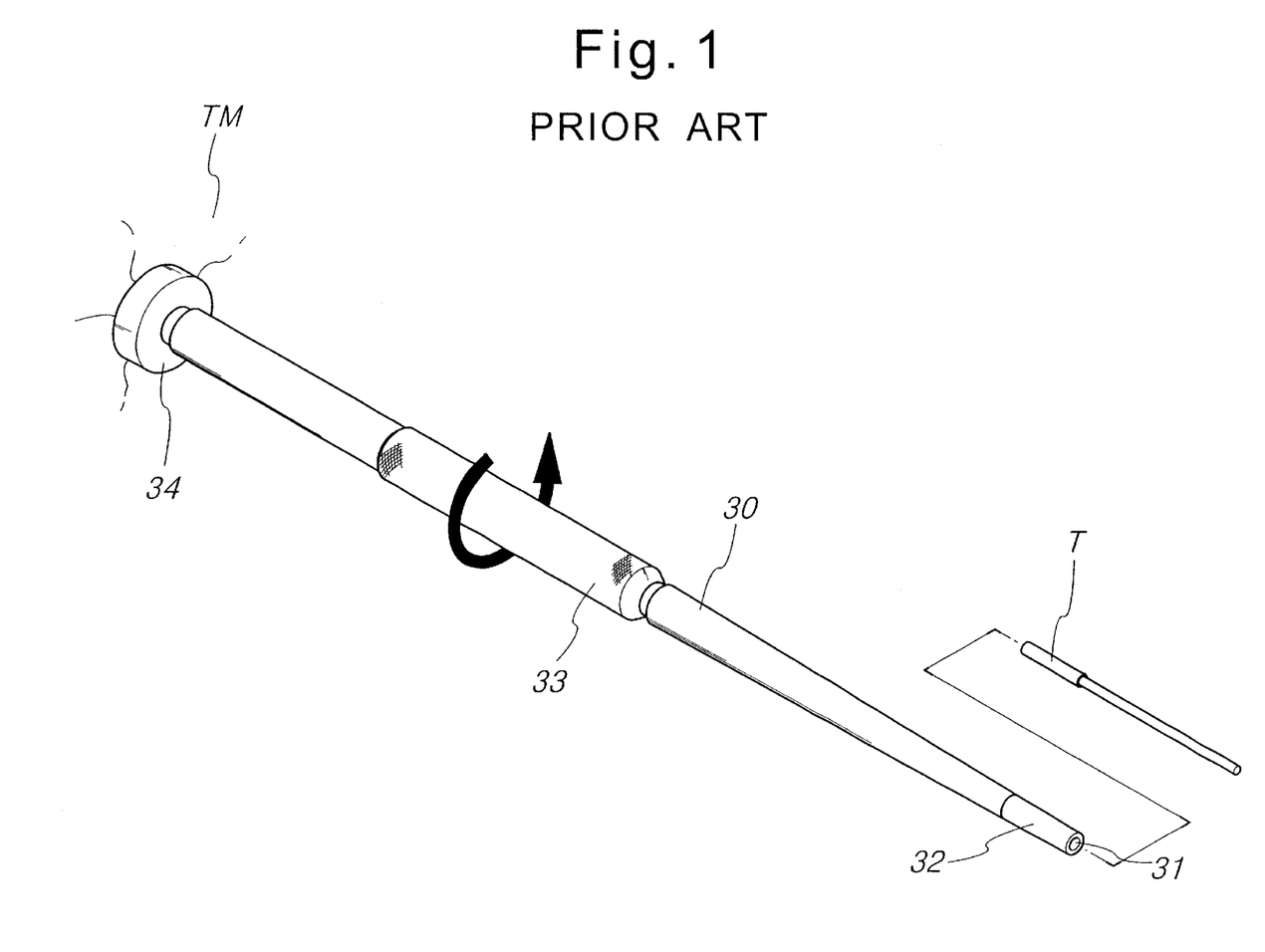
FIG. 1 is a perspective view illustrating a construction of one example of a conventional manual hand ratch reamer for a dentist.
Figure 2:
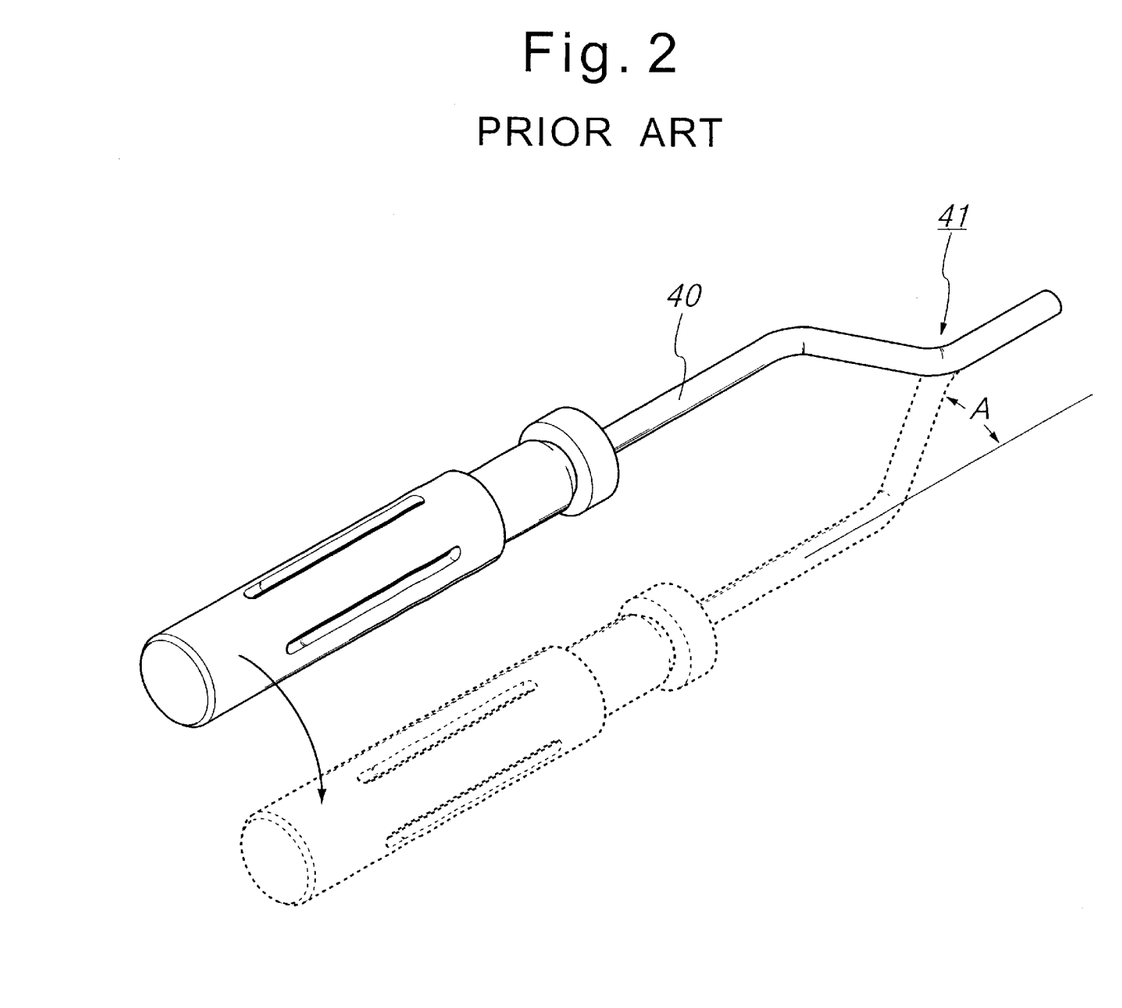
FIG. 2 is a perspective view illustrating another construction of a conventional manual hand ratch reamer for a dentist.

Two examples of a hand ratch reamer according to the conventional art are shown in FIGS. 1 and 2.

Referring to FIG. 1, there is illustrated a straight type hand ratch reamer. The straight type hand ratch reamer has a body 30 which is made of a material such as metal and has a solid configuration. The body 30 is constituted by substantially a rod-shaped element. An internally threaded portion which is not illustrated in the drawing, is found on a circumferential inner surface of one end of the body 30. The straight type hand ratch reamer further has a fixed cap 32 which is screwed into the internally threaded portion of the body 30. The fixed cap 32 can be rotated to be dismantled from the body 30. The fixed cap 32 takes, at a distal end thereof, an insertion hole 31 into which a reamer tip T can be inserted.

The body 30 includes a larger diameter section which is projectedly formed at a middle portion of the body 30 to serve as a rotating knob 33, so that convenience upon grasping the hand ratch reamer with fingers is rendered when installing the dental implant system. It is preferred that the rotating knob 33 undergoes a knurling process so as to be prevented from being slipped.

Also, a movable supporting disk 34 is secured to the other end of the body 30, which is opposite to the fixed cap 32, in a manner such that the movable supporting disk 34 can be freely moved with respect to the body 30. When the movable supporting disk 34 is pressed and rotated with fingers TM, the movable supporting disk 34 renders inserting force to the hand ratch reamer.

The conventional hand ratch reamer constructed as mentioned above and having mounted thereto the reamer tip T, is introduced into the oral cavity of a patient to form a cylindrical hole in the alveolar bone.

Another example of a conventional hand ratch reamer is shown in FIG. 2. The hand ratch reamer of this conventional example is substantially similar to the hand ranch reamer shown in FIG. 1, in respect of its construction. The hand ratch reamer of this conventional example has a body 40. The body 40 possesses a bent body section 41 which is bent by a predetermined angle A, so that operability inside the oral cavity of the patient is improved. However, an operational radius of the hand ratch reamer cannot but be considerably restricted.

The above-described conventional hand ratch reamers for a dentist suffer from defects as aforementioned above.

SUMMARY OF THE INVENTION

Accordingly, the present invention has been made in an effort to solve the problems occurring in the related art, and an object of the present invention is to provide a manual hand ratch reamer for a dentist, which is configured in a manner such that a body section of a handpiece is not rotated, and only a reamer tip section which is accommodated in an inner space defined in the handpiece, is rotated, whereby the lips of a patient are protected from possible injury.

Another object of the present invention is to provide a manual hand ratch reamer for a dentist, which is configured in a manner such that the hand ratch reamer can be bent to create a diversify of contours, whereby dental implantation surgery can be implemented in an easy manner even at a deep place inside the oral cavity of a patient.

Still another object of the present invention is to provide a manual hand ratch reamer for a dentist, which is configured in a manner such that a handpiece additionally adopts a provision for raising rotational force, whereby effort required for implementing dental implantation surgery can be reduced and thereby efficiency of dental implantation surgery can be improved, and in a manner such that a reamer tip can be easily changed with new one and a reamer tip changing time can be shortened, whereby a time required for implementing dental implantation surgery can be decreased.

In order to achieve the above objects, according to one aspect of the present invention, there is provided a manual hand ratch reamer for a dentist, which is used for forming a cylindrical hole in an alveolar bone of a patient upon implementing dental implantation surgery, characterized in that the manual hand ratch reamer for a dentist comprises a front piece body, a rear piece body and a rotating driver which are connected one with another in a manner such that the rotating driver can be independently rotated with respect to the front piece body and the rear piece body; a reamer tip locking section of the rotating driver, to which a reamer tip is secured, includes connection means which is connected to the rotating driver by passing through the inside of the front piece body; and, when the rotating driver is rotated with respect to the front piece body, the front piece body is prevented from being rotated.

According to another aspect of the present invention, the front piece body is formed as a tubular segment, as gradually decreased in its diameter toward a front end thereof, and has, at the front end thereof, an end cap on which the reamer tip locking section is rotatably supported; and the front piece body and the rear piece body are inserted into a circumferential inner wall of the rotating driver in a manner such that they are rotatably supported by the rotating driver.

According to another aspect of the present invention, the connection means comprises a driving wire which is fastened, at one end thereof, to a fastening bracket which serves as a partition wall of the rotating driver having a tubular configuration.

According to another aspect of the present invention, the driving wire comprises a solid metal wire which has a straight configuration.

According to another aspect of the present invention, the driving wire comprises a wire spring which is bent in such a way as to define therein a quadrangular space, or a wire workpiece which is formed by spirally twisting and pressing a number or steel wires in such a way as to define a polygonal cross-sectional shape.

According to another aspect of the present invention, there is provided a manual hand ratch reamer for a dentist, which is used for forming a cylindrical hole in an alveolar bone of a patient upon implementing dental implantation surgery, characterized in that the manual hand ratch reamer for a dentist comprises a front piece body, a rear piece body and a rotating driver which are connected one with another in a manner such that the rotating driver can be independently rotated with respect to the front piece body and the rear piece body; a reamer tip locking section of the rotating driver, to which a reamer tip is secured, includes connection means which is connected to the rotating driver by passing through the inside of the front piece body; when the rotating driver is rotated with respect to the front piece body, the front piece body is prevented from being rotated; and a gear assembly for raising rotating force is disposed between the rotating driver and the connection means.

According to another aspect of the present invention, the gear assembly for raising rotating force comprises an internal gear which is formed on a circumferential inner surface of the rotating driver, a planetary gear which is rotatably supported by fastening plates, and a shaft which is formed, on a circumferential outer surface thereof, with gear teeth, the internal gear, the planetary gear and the gear teeth of the shaft being meshed one with another.

According to another aspect of the present invention, the front piece body of the hand ratch reamer is formed to have a bent tube-shaped configuration which is bent at one or more points; and the driving force connection means which passes through the inside of t front piece body, comprises a wire spring.

According to still another aspect of the present invention, the front piece body which is formed to have the bent tube-shaped configuration, has a first straight portion having a length of 18 mm, a first bent portion having a length of 30 mm, a second straight portion having a length of 60 mm and a sine angle distance of the first bent portion of 20 mm.

According to yet still another aspect of the present invention an insertion securing portion which constitutes the reamer tip locking section has substantially a quadrangular cross-sectional shape in correspondence to an insertion shaft portion of the reamer tip, which has substantially a quadrangular cross-sectional shape; and the insertion seeing portion is formed to have a size which is slightly less than that of the insertion shaft portion of the reamer tip, so that the reamer tip can be secured by means of mechanical pressing force.

BRIEF DESCRIPTION OF THE DRAWINGS

The above objects, and other features and advantages of the present invention will become more apparent after a reading of the following detailed description when taken in conjunction with the drawings, in which.

DETAILED DESCRIPTION OF PREFERRED EMBODIMENTS

Reference will now be made in greater detail to a preferred embodiment of the invention, an example of which is illustrated in the accompanying drawings. Wherever possible, the same reference numerals will be used throughout the drawings and the description to refer to the same or like parts.

A manual hand ratch reamer for a dentist according to the present invention, is characterized in that it basically includes a body section which is securely maintained and prevented from being rotated, a driving wire which is rotatably disposed in the body section and serves as power transmitting means, and a driver which rotates the driving wire relative to the body section. The manual hand ratch reamer can have one or more additional component elements.

Figure 3:
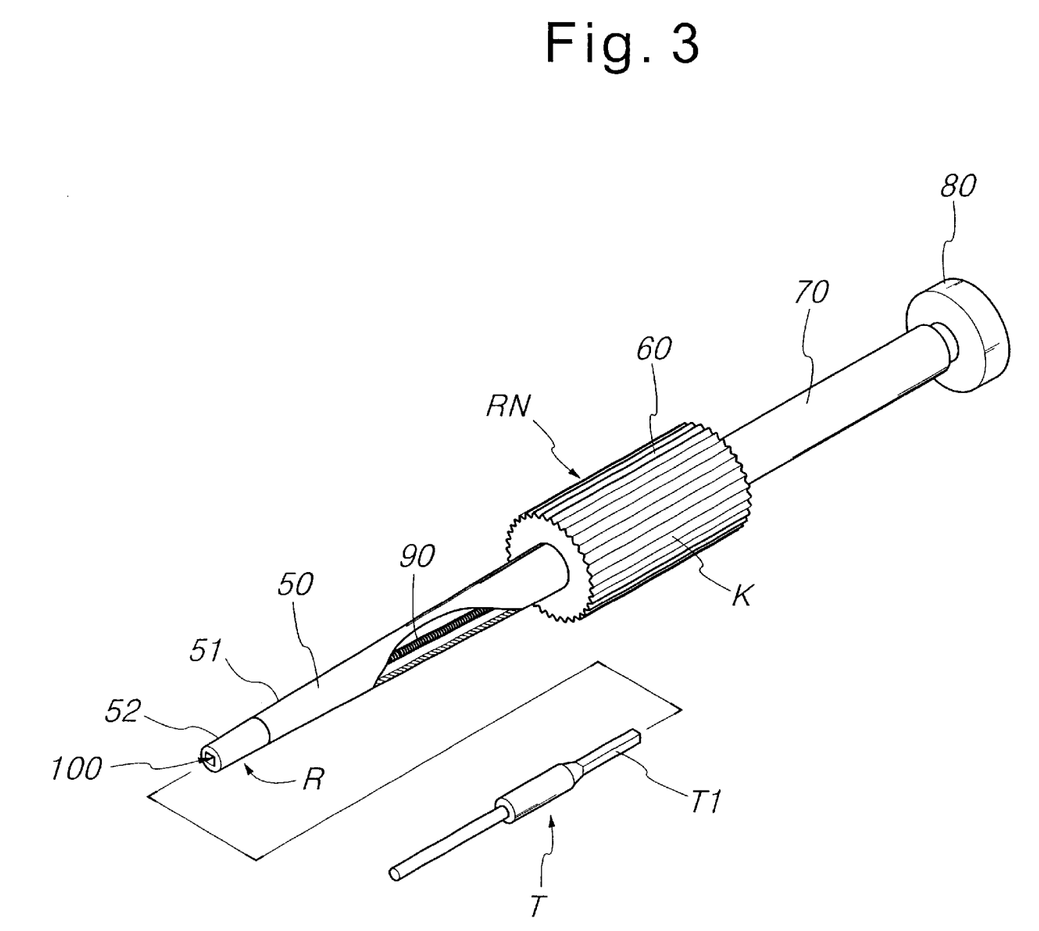
FIG. 3 is a partially broken-away perspective view illustrating an embodiment of a manual hand ratch reamer for a dentist according to the present invention.
Figure 4:
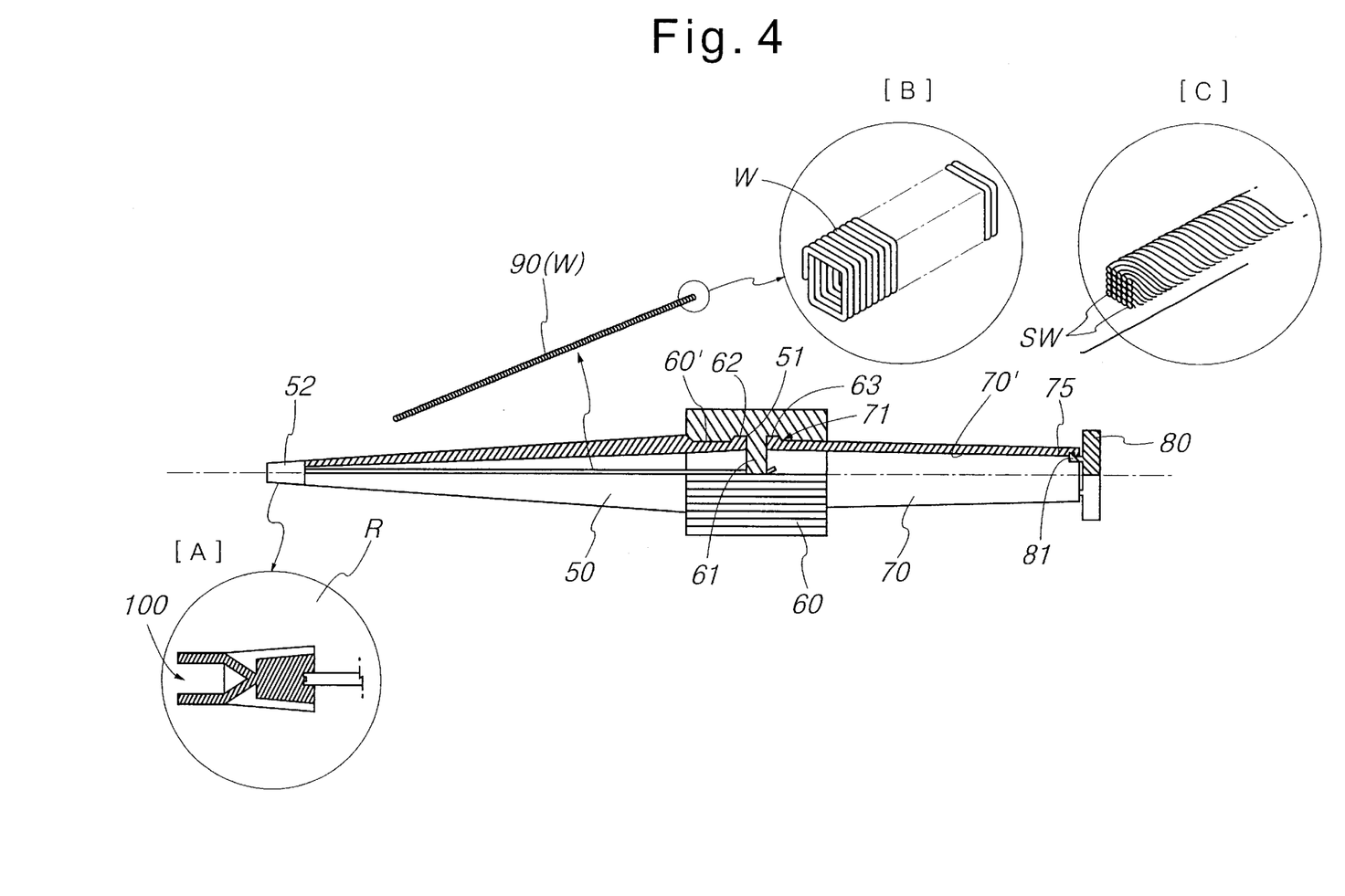
FIG. 4 is a partially enlarged half cross-sectional view illustrating the embodiment of the manual hand ratch reamer for a dentist according to the present invention, shown in FIG. 3, wherein the 'A' part represents a cross-sectional view of a fixed tip section, the 'B' part represents an exemplary partial enlarged perspective view of a wire spring, and the 'C' part represents a partial enlarged perspective view of another structure of the wire spring.

Referring to FIGS. 3 and 4, the manual hand ratch reamer RN for a dentist in accordance with an embodiment of the present invention has a front piece body 50 which constitutes a front part of the manual hand ratch reamer RN. The front piece body 50 has a tube-shaped configuration. As can be readily seen from FIGS. 3 and 4, the front piece body 50 is formed as a tube having a diameter which is gradually decreased toward a front end thereof. It is preferred that the front piece body 50 has an end cap 52 which is secured to the front end of the front piece body 50 through screwing of an internally threaded portion 51 thereof or fused to the front end of the front piece body 50.

A rotating driver 60 which has a rotating knob-shaped configuration, is mounted to a rear end of the front piece body 50, and a rear piece body 70 is supported by a rear end of the rotating driver 60. The rotating driver 60 has also a tube-shared configuration. The rotating driver 60 has a fastening bracket 61 which projects inward in a radial direction at a middle portion of the rotating driver 60. The fastening bracket 61 functions as a partition plate. The rotating driver 60 is made of a material such as metal. It is advantageous that a knurled portion K is formed on a circumferential outer surface of the rotating driver 60 so as to allow the rotating driver 60 to be easily rotated and prevent the rotating driver 60 from being slipped.

A first body step portion 51 is projectedly fitted around the rear end of the front piece body 50. The first body step portion 51 is fitted into a front circumferential inner wall 60' of the rotating driver 60 and is inserted and fastened in a first supporting ring depression 62 which is a groove defined on the front circumferential inner wall 60' of the rotating driver 60. The first body step portion 51 functions to rotatably support the front piece body 50.

By this structure, the rotating driver 60 can he freely rotated with respect to the front piece body 50.

The rear piece body 70 has also a tube-shaped configuration or a solid configuration. A second body step portion 71 is projectedly fitted around a front end of the rear piece body 70. The second body step portion 71 is fitted into a rear circumferential inner wall 60' of the rotating driver 60 and is inserted and secured in a second supporting ring depression 63 which is a groove defined on the rear circumferential inner wall 60' of the rotating driver 60. The second body step portion 71 functions to rotatably support the rear piece body 70.

As in the conventional art, a movable supporting disk 80 is secured to a rear end of the rear piece body 70 in a manner such that the movable supporting disk 80 can be supported while being freely rotated. The movable supporting disk 80 has a step portion 81. As can be readily seen from FIG. 4 which is half cross-sectional view, the step portion 81 is fitted into a third supporting ring depression 75 which is defined on a rear circumferential inner surface 70' of the rear piece body 70, and has a projecting outer race-shaped configuration.

By the just described-above structures, the rotating driver 60 can be freely rotated with respect to the rear piece body 70 and the front piece body 50.

Hereinbelow, a power transmitting relationship between the rotating driver 60 and a reamer tip locking section R of the end cap 52.

As shown in FIGS. 3 and 4, to the fastening bracket 61 which extends inward in the radial direction at the middle portion of the rotating driver 60, there is fastened one end of a driving wire 90. The driving wire 90 has. a desired length when measured in a state wherein the driving wire 90 is held free with no elastic force applied thereto. The other end of the driving wire 90 is rigidly fastened to a rear end of the reamer tip locking section R which is embedded in the end cap 52. It is preferred that the driving wire 90 is formed of a wire spring W. The wire spring W can be formed as a spring segment which is bent to define therein a quadrangular space and has a substantial length as shown in FIG. 4B by an enlarged perspective view. Otherwise, the wire spring can be formed by spirally twisting and pressing a number of steel wires SW in such a way as to define a polygonal, for example, quadrangular cross-sectional shape as shown in FIG. 4C. In the meanwhile, in the construction shown in FIG. 3, the conventional stainless steel wire can be used as it is.

As shown in FIG. 4, the reamer tip locking section R serves as a tab part which is configured so as to be embedded into and thereby secured to the end cap 52. The reamer tip locking section R has, at a front end thereof, an insertion securing portion 100 which has a configuration suitable for allowing a reamer tip T to be inserted therein, preferably, substantially a U-shaped configuration. By forming an insertion shaft portion T1 of the reamer tip T, as shown in FIG. 3, to have a quadrangular cross-section, the insertion shaft portion T1 or the reamer tip T can be inserted into the insertion securing portion 100.

More preferably, the insertion securing portion 100 which constitutes the reamer tip locking section R, is formed to have a size which is slightly less than that of the insertion shaft portion T1 of the reamer tip T, so that the reamer tip T can be securely maintained in an inserted status. By this structure, the reamer tip T can be rigidly secured to the insertion securing portion 100 while receiving mechanical tightening force. That is, the reamer tip T is substantially press-fitted into the insertion securing portion 100.

Due to the fact that a cylindrical hole forming work is performed mainly by rotating force and there is little fluctuation of the reamer tip T in an axial direction, the reamer tip T is secured by virtue of press fit as described above.

Hereinafter, working effects of the manual hand ratch reamer for a dentist in accordance with the first embodiment of the present invention will be described in detail.

The manual hand ratch reamer for a dentist according to the present invention is introduced in the oral cavity of a patient to form a cylindrical hole in the alveolar bone. Other than the conventional art, the entire manual hand ratch reamer RN is not rotated upon forming the cylindrical hole. Instead, by rotating only the rotating driver 60 while pressing and thereby grasping the movable supporting disk 80 with fingers or the palm, rotating force which is transmitted from the driving wire 90, is received by the reamer tip locking section R into which the reamer tip T is inserted. Using the rotating force, it is possible to form the cylindrical hole in the alveolar bone of the patient.

In this situation, even when the front piece body 50 of the manual hand ratch reamer RN is brought into contact with or presses the lips, or the like, of the patient, the skin of the patient can be protected from being damaged, whereby dental implantation surgery can be implemented in an easy manner.

Moreover, when the reamer tip T is changed with new one, the manual hand ratch reamer for a dentist according to the present invention does not experience continuous steps of unscrewing, dismantlement of the reamer tip T, locking of a new reamer tip T, screwing, and the like. Instead, by only removing and then inserting the insertion shaft portion T1 or the reamer tip T from and into the insertion securing portion 100 of the reamer tip locking section R, the reamer tip T can be changed with new one, whereby time can be saved upon implementing the dental implantation surgery.

Referring to FIG. 5, there is shown a manual hand ratch reamer in accordance with another embodiment, that is, a second embodiment of the present invention.

Figure 5A:
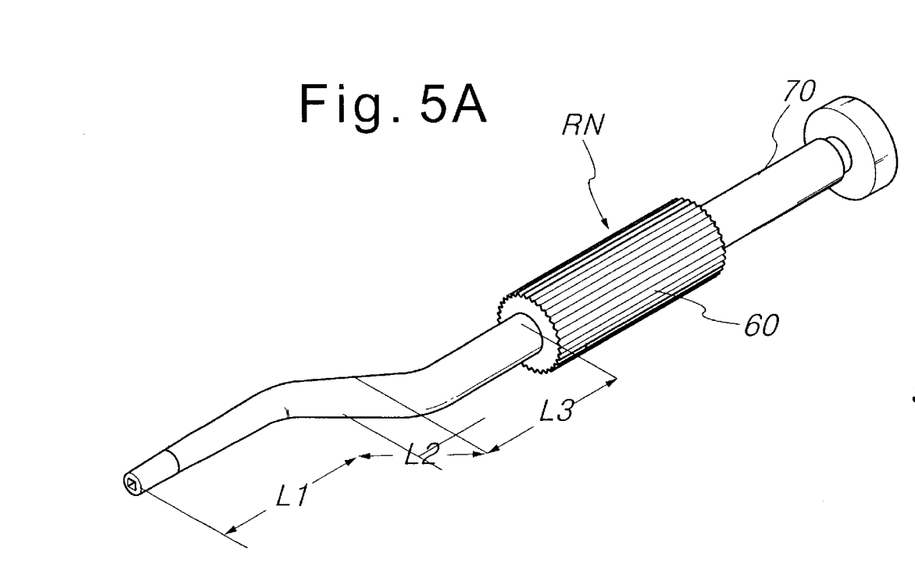
FIG. 5A is a perspective view illustrating another embodiment of a manual hand ratch reamer for a dentist according to the present invention.

When viewed as a whole, the manual hand ratch reamer RN for a dentist according to this embodiment of the present invention is bent at one or more points and thereby renders a construction which enables a reaming work, that is, a cylindrical hole forming work on the molar teeth of the patient to be performed in a more reliable manner.

In FIG. 5, the manual hand ratch reamer RN is illustrated in a state wherein a front piece body 50 forms a bent body which is bent at two points. In this case, substantially the same component elements as those of the manual hand ratch reamer according to the first embodiment of the present invention are employed in the manual hand ratch reamer according to this second embodiment of the present invention The driving wire 90 of this embodiment is not formed of a straight and solid metal but formed of a wire spring W or a wire workpiece which is formed by spirally twisting and pressing a number of steel wires SW in such a way as to define a quadrangular cross-sectional shape as shown in FIG. 4C. By this feature of this embodiment of the present invention, the wire spring W and the wire workpiece can be rotated in a state wherein they are bent at angles. Therefore, the wire spring W and the wire workpiece can transmit power while being freely rotated inside the front piece body 50 serving as the bent body which are bent at one or more points. Dimensions of the front piece body 50, which are found by experiments to be suitable therefor, are as given below:

A first straight portion L1=18 mm

A first bent portion L2=30 mm

A second straight portion L3=60 mm

A sine angle distance of the first bent portion L2=20 mm

Figure 5B:
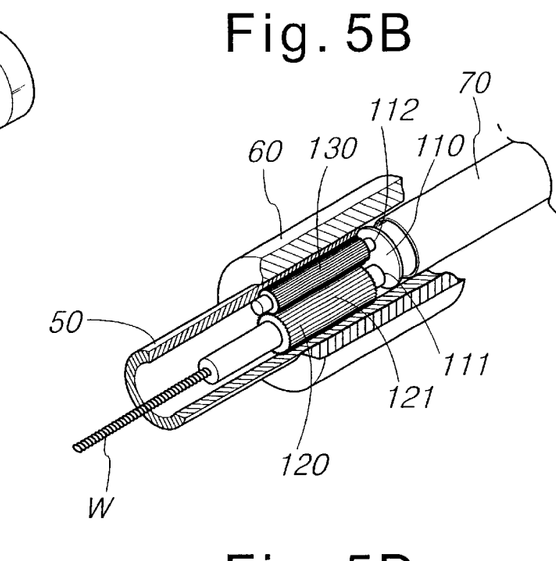
FIG. 5B is a partially broken-away perspective view illustrating the case that reduction gears are disposed in the manual hand ratch reamer.
Figure 5C:
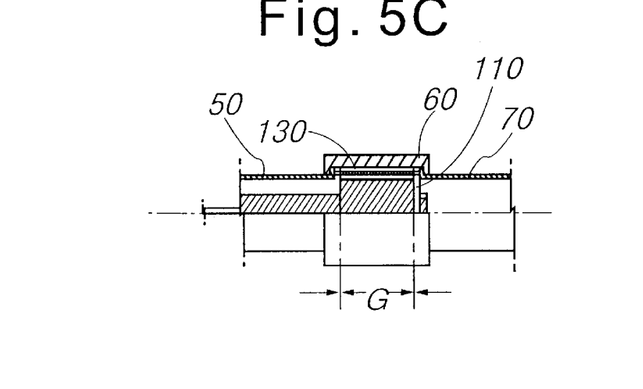
FIG. 5C is a half cross-sectional view for the manual hand ratch reamer shown in FIG. 5B.
Figure 5D:
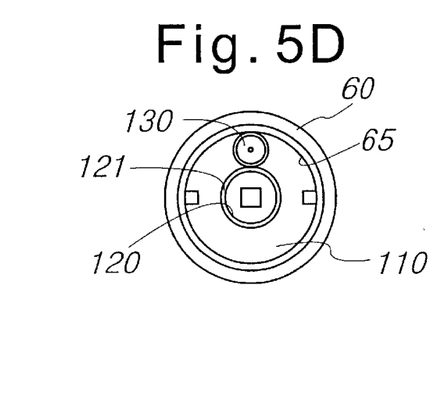
FIG. 5D is a longitudinal cross-sectional view for the manual hand ratch reamer.

Another feature of the manual hand ratch reamer according to this embodiment of the present invention, is shown in FIGS. 5B, 5C and 5D. That is to say, the manual hand ratch reamer has rotating force raising means for raising rotational driving force of the rotating driver 60. The rotating force raising means is constituted by gears which are disposed in the rotating driver 60.

An exemplary gear arrangement is shown in FIGS. 5B, 5C and 5D. FIG. 5B is a partially broken-away perspective view illustrating the case that reduction gears are disposed in the manual hand ratch reamer, with a front fastening plate omitted. Referring to FIG. 5C, the manual hand ratch reamer according to this embodiment of the present invention has fastening plates 110 which are fastened between the front piece body 50 and the rear piece body 70. One end of the wire spring W is fastened to the fastening plates 110. Both ends of a shaft 120 which is formed; on a circumferential outer surface thereof, with gear teeth 121, are supported in shaft holes 111 which are respectively defined through center portions of the fastening plates 110. Gear shaft holes 112 for supporting both awards of a planetary gear 130 are defined through upper portions of the fastening plates 110.

While the front piece body 50 and the rear piece body 70 are independently supported in the same manner as the case of the first embodiment shown in FIG. 3, in the present embodiment, they are spaced apart from each other by a distance G, the planetary gear 130 is intervened between them, and an internal gear 65 which has a width corresponding to the distance G. is formed on the circumferential inner surface 60' of the rotating driver 60.

By this structure, the internal gear 65 of the rotating driver 60, the planetary gear 130 and the gear teeth 121 of the shaft 120 are held meshed one with another.

In this structure, due to the fact that the internal gear 65 of the rotating driver 60 has a largest gear pitch and the planetary gear 130 and the gear teeth 121 of the shaft 120 have relatively small gear pitches, when the rotating driver 60 is rotated by one turn, the shaft 120 can be rotated at a high speed with force raised, and this rotating force is transmitted through the wire spring W to the reamer tip T.

As a consequence, it is possible to quickly form the cylindrical hole using relatively a low grade of force, and thereby, the dental implantation surgery can be implemented in a convenient manner and a time required therefor can be shortened.

The power transmitting mechanism can be realized using gears and gear supports which have a variety of shapes, and it is to be readily understood that this modification where made, falls within the scope of the present invention.

As a result, the manual hand ratch reamer for a dentist according to the present invention provides advantages in that, when it is used for forming a cylindrical hole in the alveolar bone of a patient, which is necessarily required upon implementing dental implantation surgery or the like, in comparison with the conventional manual hand ratch reamer, possible injury of the lips of the patient can be minimized, and a required time can be shortened. Further, since it is possible to obtain raised rotating force, convenience upon implementing the dental implantation surgery can be improved.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A manual hand ratch reamer for a dentist, which is used for forming a cylindrical hole in an alveolar bone of a patient upon implementing dental implantation surgery, characterized in that the manual hand ratch reamer for a dentist comprises a front piece body, a rear piece body and a rotating driver which are connected one with another in a manner such that the rotating driver can be independently rotated with respect to the front piece body and the rear piece body; a reamer tip locking section of the rotating driver, to which a reamer tip is secured, includes connection means which is connected to the rotating driver by passing through the inside of the front piece body; and, when the rotating driver is rotated with respect to the front piece body, the front piece body is prevented from being rotated, wherein the front piece body is formed as a tubular segment, is gradually decreased in its diameter toward a front end thereof, and has, at the front end thereof, an end cap on which the reamer tip locking section is rotatably supported; and the front piece body and the rear piece body are inserted into a circumferential inner wall of the rotating driver in a manner such that they are rotatably supported by the rotating driver.

2. The manual hand ratch reamer as claimed in claim 1, characterized in that the connection means comprises a driving wire which is fastened, at one end thereof, to a fastening bracket which serves as a partition wall of the rotating driver having a tubular configuration.

3. The manual hand ratch reamer as claimed in claim 2, characterized in that the driving wire comprises a solid metal wire which has a straight configuration.

4. The manual hand ratch reamer as claimed in claim 2, characterized in that the driving wire comprises a wire spring which is bent in such a way as to define therein a quadrangular space, or a wire workpiece which is formed by spirally twisting and pressing a number of steel wires in such a way as to define a polygonal cross-sectional shape.

5. The manual hand ratch reamer as claimed in claim 1, characterized in that the front piece body of the hand ratch reamer is formed to have a bent tube-shaped configuration which is bent at one or more points; and the connection means which passes through the inside of the front piece body, comprises a wire spring.

6. The manual hand ratch reamer as claimed in claim 5, characterized in that the front piece body which is formed to have the bent tube-shaped configuration, has a first straight portion having a length of 18 mm, a first bent portion having a length of 30 mm, a second straight portion having a length of 60 mm and a sine angle distance of the first bent portion of 20 mm.

7. The manual hand ratch reamer as claimed in claim 1, characterized in that an insertion securing portion which constitutes the reamer tip locking section has substantially a quadrangular cross-sectional shape in correspondence to an insertion shaft portion of the reamer tip, which has substantially a quadrangular cross-sectional shape; and the insertion securing portion is formed to have a size which is slightly less than that of the insertion shaft portion of the reamer tip, so that the reamer tip can be secured by means of mechanical pressing force.

8. A manual hand ratch reamer for a dentist, which is used for forming a cylindrical hole in an alveolar bone of a patient upon implementing dental implantation surgery, characterized in that the manual hand ratch reamer for a dentist comprises a front piece body, a rear piece body and a rotating driver which are connected one with another in a manner such that the rotating driver can be independently rotated with respect to the front piece body and the rear piece body; a reamer tip locking section of the rotating driver, to which a reamer tip is secured, includes connection means which is connected to the rotating driver by passing through the inside of the front piece body; when the rotating driver is rotated with respect to the front piece body, the front piece body is prevented from being rotated; and a gear assembly for raising rotating force is disposed between the rotating driver and the connection means, wherein the gear assembly for raising rotating force comprises an internal gear which is formed on a circumferential inner surface of the rotating driver, a planetary gear which is rotatably supported by fastening plates, and a shaft which is formed, on a circumferential outer surface thereof, with gear teeth, the internal gear, the planetary gear and the gear teeth of the shaft being meshed with one another.

9. The manual hand ratch reamer as claimed in claim 8, characterized in that an insertion securing portion which constitutes the reamer tip locking section has substantially a quadrangular cross-sectional shape in correspondence to an insertion shaft portion of the reamer tip, which has substantially a quadrangular cross-sectional shape; and the insertion securing portion is formed to have a size which is slightly less than that of the insertion shaft portion of the reamer tip, so that the reamer tip can be secured by means of mechanical pressing force.

* * * * *